US010980988B2

(12) United States Patent
Siegner

(10) Patent No.: US 10,980,988 B2
(45) Date of Patent: Apr. 20, 2021

(54) STENT

(71) Applicant: NOVATECH SA, La Ciotat (FR)

(72) Inventor: Georg Siegner, Berlin (DE)

(73) Assignee: NOVATECH SA, La Ciotat (FR)

( * ) Notice: Subject to any disclaimer, the term of this patent is extended or adjusted under 35 U.S.C. 154(b) by 3 days.

(21) Appl. No.: 16/609,396

(22) PCT Filed: Jul. 25, 2018

(86) PCT No.: PCT/EP2018/070218
§ 371 (c)(1),
(2) Date: Oct. 29, 2019

(87) PCT Pub. No.: WO2019/025265
PCT Pub. Date: Feb. 7, 2019

(65) Prior Publication Data
US 2020/0046950 A1 Feb. 13, 2020

(30) Foreign Application Priority Data
Aug. 1, 2017 (DE) .................... 10 2017 117 439.7

(51) Int. Cl.
A61M 27/00 (2006.01)
A61F 2/90 (2013.01)

(52) U.S. Cl.
CPC ............. A61M 27/002 (2013.01); A61F 2/90 (2013.01); A61M 2205/0216 (2013.01); A61M 2210/1053 (2013.01)

(58) Field of Classification Search
CPC ........ A61M 27/002; A61M 2205/0216; A61M 2210/1053; A61F 2/885; A61F 2/89;
(Continued)

(56) References Cited

U.S. PATENT DOCUMENTS

2002/0169498 A1 11/2002 Kim et al.
2015/0045875 A1 2/2015 Hingston et al.
(Continued)

FOREIGN PATENT DOCUMENTS

EP 1849440 A1 10/2007
EP 2918251 A1 9/2015
EP 3158977 A1 4/2017

OTHER PUBLICATIONS

International Search Report issued by the European Patent Office in International Application PCT/EP2018/070218.
(Continued)

Primary Examiner — Philip R Wiest
(74) Attorney, Agent, or Firm — Henry M. Feiereisen LLC

(57) ABSTRACT

A stent has a center length section, two end sections, and an elastically deformable woven wire mesh, which enables the stent to expand from a small diameter to a larger diameter, with the diameter of the end sections being larger than in the center length section in the expanded state. The wire extends in a zig-zag manner from an outer end of one end section toward the outer end of the other end section, and back in a zig-zag manner to the one end section. The peripheral direction of the woven wire changes at the transition from an end section to the center length section, such that the wire intersects on the return path to the one end section in the center length section and overall forms an 8-shaped loop having two closed eyes, wherein a plurality of interconnected loops are arranged offset to each other over the circumference.

8 Claims, 3 Drawing Sheets

(58) Field of Classification Search
CPC ........ A61F 2/90; A61F 2/95; A61F 2002/045; A61F 2002/8486; A61F 2230/001; A61F 2230/0039; A61F 2230/0069; A61F 2240/001; A61B 17/1114; A61B 2017/1139
See application file for complete search history.

(56) References Cited

U.S. PATENT DOCUMENTS

2016/0213498 A1* 7/2016 Wang ................. D04C 1/06
2016/0361180 A1  12/2016 Vong et al.
2017/0014133 A1* 1/2017 Han ................... A61F 2/90

OTHER PUBLICATIONS

German Search Report dated Feb. 15, 2018 with respect to counterpart German patent application 10 2017 117 439.7.
Translation of German Search Report dated Feb. 15, 2018 with respect to counterpart German patent application 10 2017 117 439.7.

* cited by examiner

STENT

CROSS-REFERENCES TO RELATED APPLICATIONS

This application is the U.S. National Stage of International Application No. PCT/EP2018/070218, filed Jul. 25, 2018, which designated the United States and has been published as International Publication No. WO 2019/025265 A1 and which claims the priority of German Patent Application, Serial No. 10 2017 117 4391, filed Aug. 1, 2017, pursuant to 35 U.S.C. 119(a)-(d).

BACKGROUND OF THE INVENTION

The invention relates to a stent.

An endoscopically implantable stent for placement in a cavity of the body can, for example, produce a connection between the stomach and a pseudocyst. For this purpose, a small hole is cut in the stomach wall and in the wall of the pseudocyst. The insertion system for the stent is pushed through this hole, and the stent is placed in the hole. The stent has two spread-open sides (flanks) and a cylindrical central part. It is therefore similar in its contour to an hourglass. The flanks have the function of preventing the stent from slipping out from the implantation site. The cylindrical part keeps the passage between the pseudocyst and the stomach open, so that material from the pseudocyst can flow off. The cylindrical part is placed in the hole of the stomach wall and of the pseudocyst, while the flanks are placed on the one hand in the stomach and on the other hand in the pseudocyst. Since the prepared hole for insertion of the stent should be as small as possible, the diameter of the cylindrical part of the stent is compressed to be very small directly after the implantation, on account of the small diameter of the hole. In the conventional weaving of a wire framework of the stent, this has the effect that the flanks of the stent are also compressed, i.e. are reduced in diameter. This reduction in diameter can go so far that the stent is able to slip out from the implantation site. The straight weaving of the stents unfortunately has the effect that a stent, when compressed at one location, likewise decreases in diameter at adjacent locations. Although this is helpful in manual crimping, it can lead to problems at the implantation site in the case of the stents described above.

Proceeding from this, the object of the invention is to make available a stent which has a central section of smaller diameter and end sections of greater diameter and which permits compression of the central part without reducing the diameter of the end sections to the same extent.

SUMMARY OF THE INVENTION

This object is achieved in a stent having a central length section and two end sections, and having an elastically deformable woven wire mesh, which enables the stent to expand from a small diameter to a larger diameter, wherein the diameter of the end sections is larger than in the central length section in the expanded state, wherein the wire runs in a zigzag shape, coming from an outer end of one end section toward the outer end of the other end section, and back from there in a zigzag shape to the original end section, wherein the circumferential direction of the woven wire changes at the transition from each end section into the central length section, such that the central the wire crosses itself in the central length section on the return path to the first end section and overall forms an 8-shaped loop having two closed eyes, wherein a plurality of interconnected loops are arranged offset to each other over the circumference.

The dependent claims relate to expedient refinements of the invention.

The stent according to the invention has a central length section, which is preferably cylindrical. The central length section is adjoined by two end sections. The stent has a supporting framework composed of a deformable woven wire mesh. The stent is in particular self-expanding. It can be surrounded by a cover made of plastic that is expanded together with the supporting framework. The cover moreover keeps the woven wire mesh in shape in the sense that adjoining wires are connected to each other via the flexible cover. The cover follows the movement of the supporting wire framework.

The stent according to the invention can expand in diameter after implantation. Accordingly, it initially has a small diameter. In the expanded state, the stent has a diameter which is greater in the region of the end sections than in the central length section. The stent therefore has more or less the shape of a dumbbell or hourglass. The end sections can also be designated as flanks which are provided for holding the stent in a wall, wherein the stent passes through an opening in the wall, and wherein each flank is arranged in a lumen bordering the wall.

According to the invention, provision is made that the woven wire runs in a zigzag shape, coming from an outer end of one end section toward the outer end of the other end section, and back from there to the original end section. The return path is also zigzag-shaped. The turning points of the zigzag shape are each arranged at the transition from one end section into the central length section, such that the circumferential direction in which the woven wire is positioned changes at the transition from an end section to the central length section. This has the effect that the wire crosses itself in the central length section on the return path to the first end section. This results in an 8-shaped loop having two closed eyes, but with a polygonal contour. In contrast to a straight weave in which the circumferential direction of the woven wire remains the same, the special zigzag weaving technique has the effect that the movement upon compression of the cylindrical central length section is deflected via the wire mesh into the end sections, triggering a movement there in the opposite direction. In the region of the end sections, this causes radial widening, i.e. spreading, of the outer ends. The spreading in turn causes the stent to be locked securely in the passage, such that the stent is held much more securely and cannot slip out of the passage.

The weave according to the invention decouples the movement of the end sections from the central length section in the sense that the movement, upon reduction of the diameter at the center, does not take place in the same direction but in the opposite direction. The funnel-shaped end sections of the stent deploy to their normal size directly upon implantation. The special weave has the effect that, upon compression of the central part, the end sections of the stent open to an even greater extent, which is not possible with a straight weave.

It is considered advantageous if the zigzag-shaped course of the wire on the return path from the second end section to the first end section is the mirror image of the preceding zigzag-shaped course of the wire on the outward path from the first end section to the second end section. The mirror-symmetrical configuration has the effect that the adjoining regions of the end sections deform identically. The oppositely directed movement of the stent in the end sections is particularly uniform if the zigzag-shaped weave is arranged with mirror symmetry.

The invention assumes that the weave is as it were endless and extends from a start point at an outer end of the first end section to an end point, which can be identical to the start point. The weave pattern with the 8-shaped loops is repeated in an offset manner over a defined circumferential range. Where reference is made to zigzag-shaped courses that intersect each other, this refers to the course of the wire from one end section to the other end section and back again. Thereafter, the same pattern repeats itself. By means of overlaps and intersection points, a sufficiently dense and load-bearing woven wire mesh is created. The pattern can repeat itself every 30° for example. Accordingly, said start points and deflection points from loop to loop are offset by 30° from each other. Narrower or wider divisions are of course possible.

In an advantageous refinement of the invention, the enclosed angle between two branches of the wire, at the transition from an end section to the central length section, measures less than 90° in a developed view of the stent. It is an acute angle. For the acute angle, it is necessary that the wire in the first end section already runs toward the first deflection point at an acute angle with respect to the longitudinal axis.

In relation to the circumferential direction, the reverse that the wire makes after the first deflection point in the central length section is greater than the circumferential range that the wire covers in the first end section. In its third branch of the zigzag-shaped course, the wire is accordingly oriented again in the circumferential direction. The wire is deflected at the outer end of the second end section. By virtue of the desired axial symmetry, the course of the wire on the return path is the exact reverse of the outward path. Accordingly, the last branch on the return path likewise has mirror symmetry to the first branch of the outward path. To provide an offset of the loops at the circumference, the first branch of the outward path and the last branch of the return path cross each other in the first length section. The end point of the first loop is therefore offset in the circumferential direction. Beginning from this start point, the next loop can then be laid, for example offset by 30° in the circumferential direction.

In contrast to a substantially straight or orbital winding, an individual loop extends over a relatively narrow circumferential range, which is at least smaller than 360°. In the central length section, the wire preferably extends over a circumferential range of more than 90°, in particular over a circumferential range of 115°. In this way, in the central length section, sufficient coverage and preferably a large overlap with adjacent loops is achieved, such that the radially outwardly directed forces keeping the stent open are sufficiently great on account of a suitably narrow weave. The greater the circumferential range over which the wire extends in the central length section, the denser is the weave.

The end sections and therefore the deploying flanks are preferably longer than the central length section in a developed view. This means that the flanks in the expanded state can deploy farther than the central length section, assuming that all of the length sections stretch uniformly. A shorter central length section means that the wire in the central length section has a greater pitch, with respect to the circumferential direction, than in the two end sections. This is the preferred embodiment. Despite the preferably longer end sections and the shorter central length section, the wire in the central length section should be longer than in each of the adjacent end sections. This feature too contributes to there being many intersections in the central length section, such that the weave density is particularly great here. In contrast to less dense weaves, the stent thus acquires the property of being more difficult to compress. Its holding force is greater. As has already been mentioned, it is considered to be particularly preferable if adjacent or successive loops or zigzag-shaped windings are offset relative to each other by 30° in the circumferential direction. If at the same time the central length section extends over 115°, this has the effect that each central branch of the zigzag-shaped woven wire is intersected by six further central branches which run in the opposite direction. Since this applies to each of the branches in the central length section, a very dense weave pattern is obtained there.

The number of the intersection points in the first and second length sections is smaller, since the wire there has a lesser pitch and therefore also extends over a smaller circumferential range. The weave is more open, more flexible and not so dense, but this is entirely sufficient and even desirable for the function of a flank of an hourglass-shaped stent.

BRIEF DESCRIPTION OF THE DRAWING

The invention is explained in more detail below on the basis of an illustrative embodiment shown schematically in the drawings, in which.

DETAILED DESCRIPTION OF PREFERRED EMBODIMENTS

Figure 1:
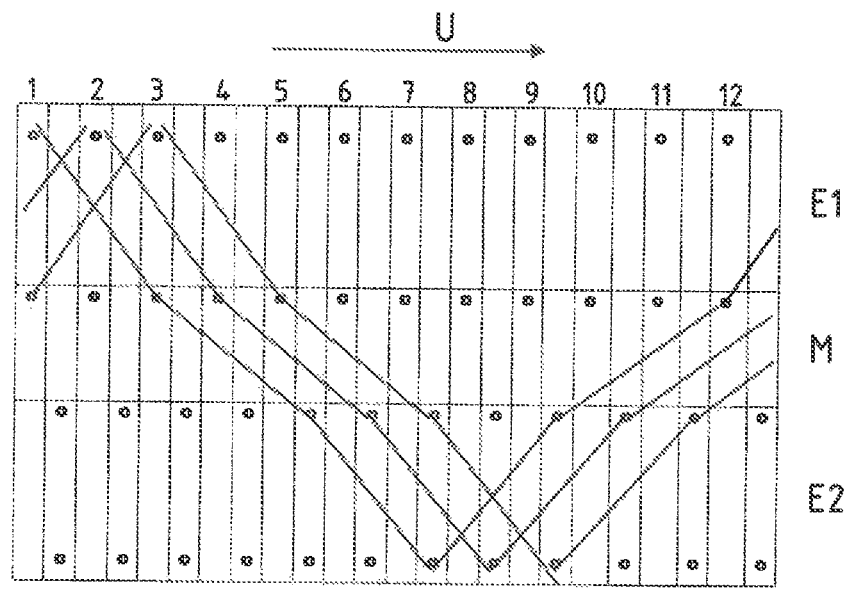
FIG. 1 shows the weave pattern of a pseudocyst stent in a developed view (prior art)
Figure 2:
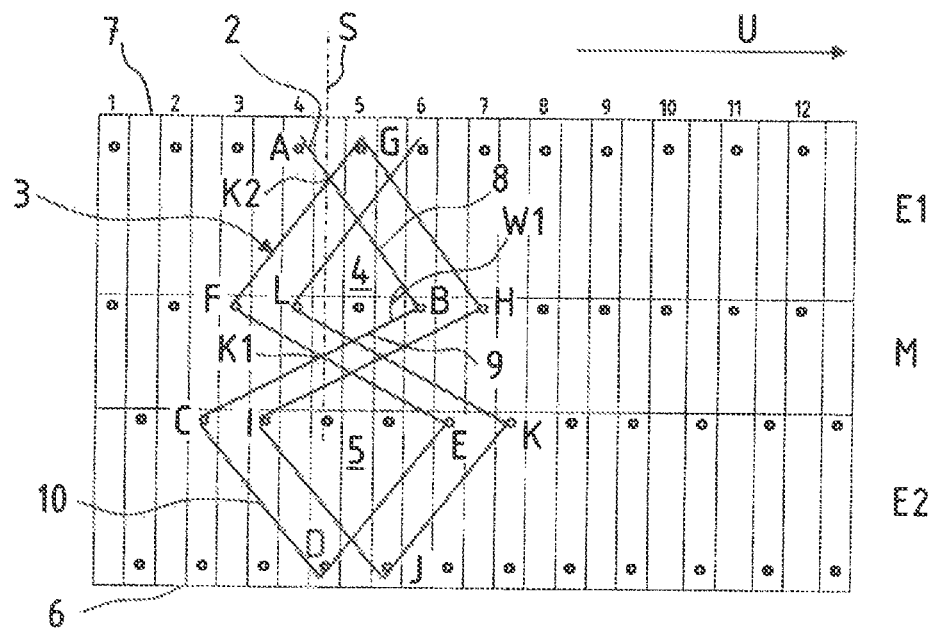
FIG. 2 shows a developed view of a weave pattern, according to the invention, of a pseudocyst stent.

FIG. 1 shows the weave pattern of a pseudocyst stent 1 as prior art. The Illustration is a developed view of the stent 1. The associated stent 1 is shown on the left in each of FIGS. 5 to 10. The stent 1A according to the invention is shown on the right in the image plane of each of FIGS. 5 to 10. The associated weave pattern of the stent Zar according to the invention is shown in FIG. 2.

Figure 3:
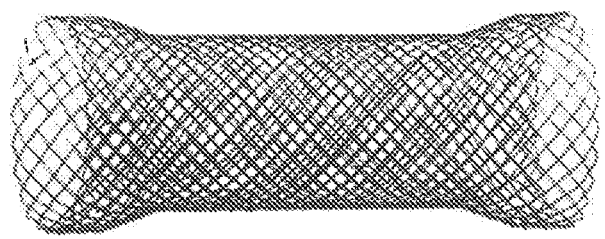
FIG. 3 shows a woven stent in a side view (prior art)
Figure 4:
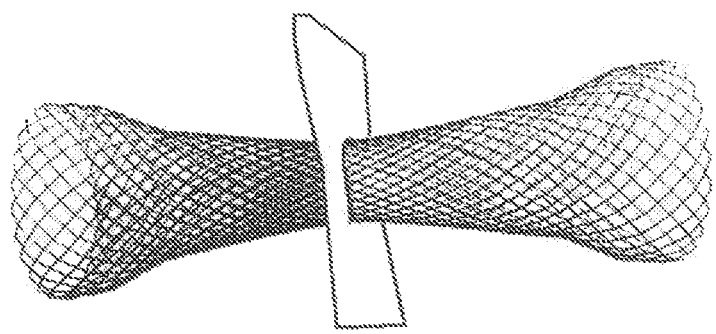
FIG. 4 shows the stent from FIG. 3, compressed at the center.

Firstly concerning the prior art:

FIG. 3 shows a woven stent of the prior art. The shape of the stent is substantially cylindrical. It has a central length section and two shorter end sections, wherein the end sections are wider in diameter. This stent is in principle woven according to the weave pattern of FIG. 1. FIG. 4 shows the stent from FIG. 3 when compressed at the center. This leads to a diameter reduction in immediate proximity to the central region, but also over almost the entire length of the stent. It will be noted that the diameter reduction decreases toward the ends. However, substantially the entire central length section is reduced in diameter, even though there is only a punctiform loading at the center.

The weave pattern that brings about this effect is shown in the developed view in FIG. 1. The developed view shows three length sections of the stent. There are two end sections E1, E2 and, between the end sections E1, E2, a slightly shorter central length section M. The central length section M is approximately only half as long as an end section E1, E2. The wire runs consequently in the circumferential direction U, i.e. in the direction of the arrow indicated. The numbers 1 to 12 designate individual sections of the circumference U. An angle range of 30° extends between two sections. It will be noted that the wire weave never changes direction, as viewed over the circumference. Even though the pitch of the wire in the central length section M changes in the sense that it is slightly greater than in the adjacent end sections E1, E2, the wire is always guided onward in one direction over the circumference U. The wire is always guided from left to right in the image plane. At the wire intersection points, the wires are guided once over each other and once under each other such that a weave is obtained.

Figure 5:
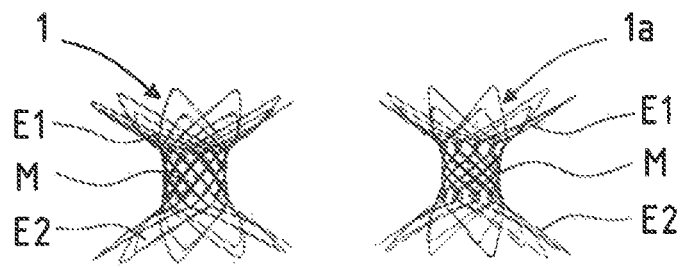
FIG. 5 shows two stents (prior art on the left, according to the invention on the right)
Figure 6:
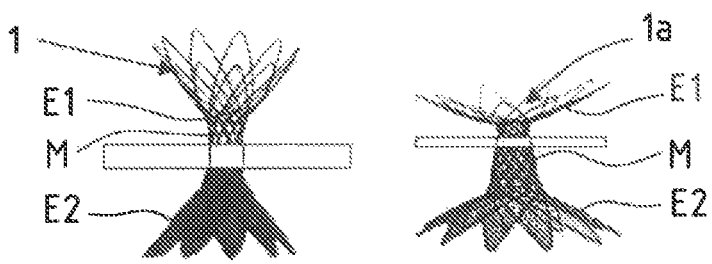
FIG. 6 shows the stents from FIG. 5, partially in the compressed state.

This stent 1, as shown on the left in FIG. 5, has the property whereby the end sections E1, E2, configured as it were as flanks, flatten out upon insertion into a wall opening of small diameter, i.e. upon compression of the central length section M. This is shown in FIG. 6. The same stent 1 is shown in the relaxed state in FIG. 5. The flanks or end sections E1, E2 have a steeper (greater) clearance angle with respect to the longitudinal axis of the stent. Upon compression of the central section, the clearance angle is substantially smaller, such that the stent 1 can more easily slip out of the opening.

In the relaxed state, the stent 1a according to the invention in FIG. 5 (shown on the right) looks exactly like the stent 1 from the prior art (shown on the left) in terms of its contour. The reference signs mentioned in relation to the stent 1 already explained are used hereinbelow for substantially identical components of the stent 1a according to the invention. In particular, the central length section M has the same length. The flank angles of the end sections E1, E2 are also identical.

FIG. 6 shows that the stent 1a according to the invention, which is likewise compressed in its central length section M, has, in the implanted situation, a behavior that is entirely different than that of the stent on the left in the image plane. The flank angles have not become smaller, and instead they are even greater compared to the relaxed starting position according to FIG. 5. This is particularly clear from the upper end section E1 in the image plane of FIG. 6. Said end section E1 has deployed to almost 90°, such that the stent 1a cannot in any way slip through the symbolically indicated opening. In this illustrative embodiment, the constriction shown in FIG. 6 lies closer to the upper end section E1 than to the lower end section E2. Therefore, the end section E1 has also fanned out farther than the other end section E2. This means that the constriction has a greater influence on the fanning-out of the end sections the closer the constriction is adjacent to one of the end sections E1, E2. The stent is configured with mirror symmetry in relation to its central transverse plane, such that the same effect would also arise if the stent 1a had been inserted the other way round into the opening or narrowing, or if the stent slips with its second end section E2 closer to the opening. It will be noted that the stent 1a according to the invention therefore has better properties in the installation position if it is constricted regionally or all along the central length section. In this case too, the constrictions would have a positive influence on the clearance angles of the end sections E1, E2, since the end sections are set more steeply. Without constrictions, its properties are just as good as those of the stent 1 according to the prior art.

Figure 7:
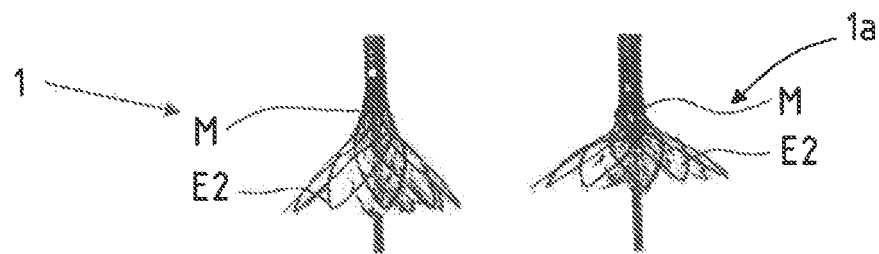
FIG. 7 shows the release of two stents (prior art on the left, weave according to the invention on the right)

FIGS. 7 to 10 show how the stent 1 according to the prior art and the stent 1a according to the invention are released. In FIG. 7, only the end section E2 first emerging is released. It will already be noted here that the constriction still present in the central length section M acts on the end section E2 according to the invention in such a way that the latter has a steeper clearance angle to the longitudinal axis and therefore spreads out farther over a shorter length than the comparable end section E2 of the stent 1 according to the prior art.

Figure 8:
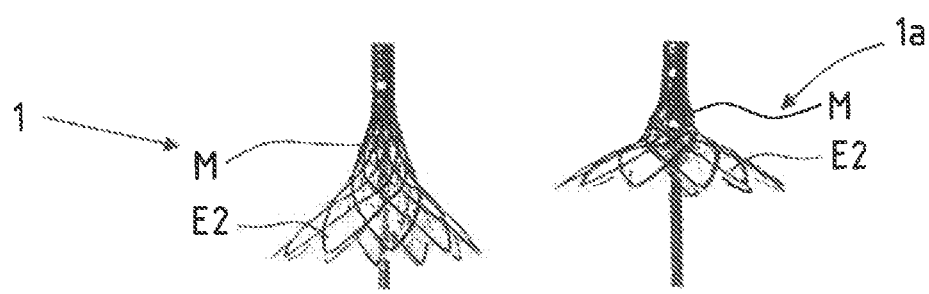
FIG. 8 shows the stents from FIG. 7, after the stents have been released by half.

FIG. 8 shows the two stents 1, 1a, which have each been released by half. Here too, it will again be clearly seen that the end section E2 of the stent 1a according to the invention, shown on the right in the image plane, has fanned out much more steeply than in the case of a stent 1 according to the prior art.

Figure 9:
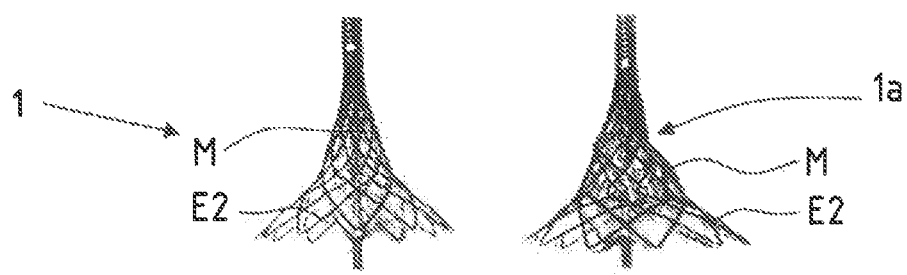
FIG. 9 shows the stents from FIG. 7, after they have been released by three quarters of their length.

FIG. 9 shows the two stents 1, 1a after they have been released by three quarters. Since the region directly adjacent to the end section E2, i.e. the central length section M, is held only by the as yet unreleased end section E1 and is therefore less strongly compressed, the end section E2 is also no longer fanned out so steeply. It will be clearly seen, however, that the central length section M, considered as a whole, has a greater external diameter than the stent 1 according to the invention. This means that the still compressed part of the as yet unreleased end section E1 of the stent 1a acts to a much lesser extent on the diameter of the central length section than is the case in the prior art. In terms of the way in which they influence the contours of each other, the two end sections E1, E2 and the central length section M are more strongly decoupled from each other than is the case in the stent 1 according to the prior art.

Figure 10:
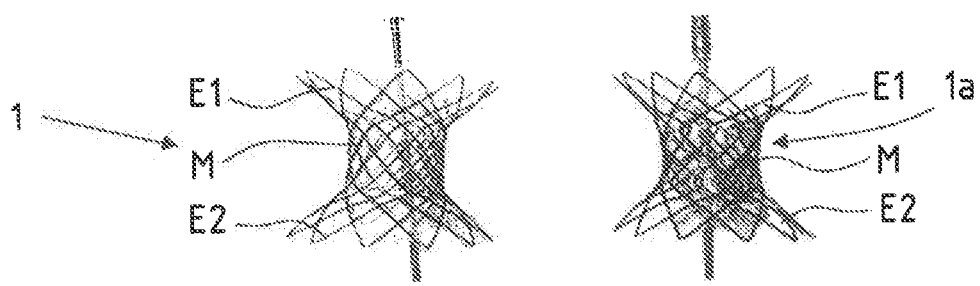
FIG. 10 shows the stents from FIG. 7 after complete release.

The complete release of the stents 1, 1a, as shown in FIG. 10, results in the substantially identical outer contour despite the other weave pattern. Since the lengths, proportions and diameters of the individual length sections of the stents 1, 1a are identical, substantially the same outer contour is obtained. However, as a result, the stent 1a according to the invention, shown on the right in the image plane, has the better properties in the implanted position, since the stent is more effectively prevented from slipping out from the implantation site than in the case of a stent according to the prior art.

Details of the weave pattern are explained below with reference to FIG. 2. The wire is guided in a zigzag shape via a plurality of deflection points A-L. A substantially 8-shaped loop 3 can be seen which has two closed eyes 4, 5. FIG. 2 shows two of these 8-shaped loops 3 next to each other, because the weave pattern repeats itself in an offset manner in the circumferential direction U. The weave pattern can also be designated as a zigzag-shaped pattern. The zigzag shape is the result of the fact that the wire 2, coming from the first end section E1, is guided from the first deflection point A (start point) to the second deflection point B obliquely with respect to the circumferential direction U. At the deflection point B, which is located at the boundary to the central length section M, the weave direction is reversed and the wire 2 runs counter to the circumferential direction U from the second deflection point B to the third deflection point C at the boundary to the second end section E2. Viewed in the circumferential direction, this reverse step is even greater than the circumferential distance from the deflection point A to the deflection point B. In this illustrative embodiment, the wire 2 has covered 60° from deflection point A to deflection point B, whereas a circumferential range of 115° has been covered on the reverse path from deflection point B to deflection point C. Finally, the wire 2 runs in the circumferential direction from the deflection point C to the next deflection point D at the outer end 6 of the second end section E2. One half of the 8-shaped loop 3 is thus described. Starting from the deflection point D, the wire 2 is guided back again in a mirror image to the first end section E1. Since an angle of 60° has been covered from the deflection point C to the deflection point D, the wire 2 is now guided back, likewise offset by 60° in the circumferential direction, to the deflection point E at the transition to the central length section M. From there, it reverses again, counter to the circumferential direction U, to the next deflection point F at the transition to the first end section E1. From there, the wire 2 again runs in a mirror-image arrangement to the outermost end 7 of the first end section E1 (deflection point G). The deflection point G is the end point of the first loop 3. Since start point and end point are not identical, the next loop 3 begins at a 30° offset corresponding to the circumferential distance of the deflection points A and G at the outermost end 7 of the first end section E1. The deflected. The list therefore the start point for the second loop. This weave patter repeats itself along the deflection points H to L until the wire 2, after 360°, arrives again at the first deflection point A. The stent 1 is then completely woven.

In a manner not shown in detail, the wire at the intersection points of the onward course is guided over and under, resulting in a woven wire mesh. According to the invention, provision is made that, on account of the 8-shaped loop 3, an intersection point K1 lies in the central length section M. A further intersection point K2 arises in the first end section E1, since first deflection point A and last deflection point G are not congruent. The axis of symmetry S through the two intersection points K1, K2 runs parallel to the longitudinal axis, such that the loop 3 is as it were arranged axially parallel to the stent.

FIG. 2 moreover shows that the lower eye 5 of the loop 3, as seen in the image plane, is larger than the upper eye 4. This is due to the fact that the deflection points C, E between the central length section M and the second end section E2 lie farther apart from each other than at the transition to the first end section E1. However, the loop 3 has mirror symmetry with respect to the mirror axis S through the intersection points K1 and K2. At the transition from one end section E1 to the central length section M, the zigzag-shaped loop 3 encloses an angle W1 which is smaller than 90°. Here, the angle W1 is indicated for example between the first branch 8 and the second branch 9, wherein the first branch 8 extends between the deflection points A and B and the second branch extends between the deflection point B and C. Both branches 8, 9 run in a straight line between successive deflection points A-L. The zigzag shape of the stent 1a therefore relates to the course of the wire 2 between the deflection points A-L.

Since the wire 2 in the central length section M covers a greater circumferential range than in an end section E1, E2, the wire 2 in the central length section M has a greater pitch with respect to the circumferential direction U. The enclosed angle (not shown in detail) between the second branch 9 and the arrow, which points in the circumferential direction U, is therefore smaller than the angle between the other branches of the wire 2 in the end sections E1, E2 and the circumferential direction U. Therefore, the branch 9 in the central length section M is also longer than a branch 8 in the first end section E1 or a corresponding branch 10 in the second end section E2.

FIGS. 6 to 10 show gray shading between the individual loops of the stents 1, 1a. This is intended to illustrate that the wire is embedded in a sheath which is supported by the wire braid and which follows the movement of the wire 2. The sheath is made in particular of plastic. The wire is made of a biocompatible material, in particular a shape-memory alloy, for example nitinol.

What is claimed is:

1. A stent, comprising:
  a central length section;
  two end sections having a diameter; and
  an elastically deformable woven wire mesh configured to enable the stent to expand from a first diameter to a second diameter which is greater than the first diameter, with the diameter of the end sections exceeding a diameter in the central length section, when the wire mesh is expanded, said wire mesh having a woven wire which runs in a zigzag shape from an outer end of one of the end sections toward an outer end of the other one of the end sections, and back in a zigzag shape to the one of the end sections, wherein a circumferential direction of the woven wire changes at a transition from each of the end sections into the central length section, such that the woven wire crosses itself in the central length section on a return path to the one of the end sections and forms an 8-shaped loop having two closed eyes, with a plurality of interconnected loops being arranged offset to each other over a circumference of the woven wire.

2. The stent of claim 1, wherein a zigzag-shaped course of the wire on the return path from the other one of the end sections to the one of the end sections is a mirror image of a preceding zigzag-shaped course of the wire on an outward path from the one of the end sections to the other one of the end sections, with a mirror axis running parallel to a longitudinal direction of the stent.

3. The stent of claim 1, wherein the wire has two branches which define an angle at the transition from a corresponding one of the end sections into the central length section, said angle measuring less than 90° in a developed view of the stent.

4. The stent of claim 1, wherein the wire in the central length section has a pitch which with respect to the circumferential direction is greater than a pitch in the two end sections.

5. The stent of claim 1, wherein the wire extends in the central length section over a circumferential range of more than 90°.

6. The stent of claim 1, wherein the wire has in the central length section a length which is greater than a length in each of the end sections.

7. The stent of claim 1, wherein mutually adjacent windings of the 8-shaped loop are offset relative to each other by 30° in the circumferential direction.

8. The stent of claim 1, further comprising a sheath, said woven wire mesh being embedded in a sheath.

* * * * *

UNITED STATES PATENT AND TRADEMARK OFFICE
CERTIFICATE OF CORRECTION

PATENT NO. : 10,980,988 B2  
APPLICATION NO. : 16/609396  
DATED : April 20, 2021  
INVENTOR(S) : Georg Siegner Page 1 of 1

It is certified that error appears in the above-identified patent and that said Letters Patent is hereby corrected as shown below:

On the Title Page

Under (71) Applicant:  
Replace "La Ciotat (FR)" with -- La Ciofat Cedex (FR) --.

Under (73) Assignee:  
Replace "La Ciotat (FR)" with -- La Ciotat Cedex (FR) --.

In the Specification

In Column 1, Line 11:  
Replace "10 2017 117 4391" with -- 10 2017 117 439.7 --.

Signed and Sealed this  
Sixth Day of July, 2021

Drew Hirshfeld  
*Performing the Functions and Duties of the*  
*Under Secretary of Commerce for Intellectual Property and*  
*Director of the United States Patent and Trademark Office*